United States Patent [19]

Wellington

[11] 4,119,491
[45] Oct. 10, 1978

[54] ENZYME-FILTRATION CLARIFICATION OF XANTHAN GUM POLYMER SOLUTION

[75] Inventor: Scott L. Wellington, Houston, Tex.

[73] Assignee: Shell Oil Company, Houston, Tex.

[21] Appl. No.: 797,093

[22] Filed: May 16, 1977

[51] Int. Cl.² .............................. C12D 13/04
[52] U.S. Cl. .............................. 195/7; 210/2; 210/12; 195/31 P; 252/8.55 D; 536/114
[58] Field of Search .............. 210/2, 11, 18, 12; 195/4, 7, 31 P; 536/1, 114; 252/8.55 D; 166/246

[56] References Cited

U.S. PATENT DOCUMENTS

| | | | |
|---|---|---|---|
| 3,476,741 | 11/1969 | Jonas | 536/114 |
| 3,516,983 | 6/1970 | Colegrove | 195/31 P |
| 3,711,462 | 1/1973 | Abdo | 536/1 |
| 3,862,003 | 1/1975 | Okuyama et al. | 195/7 |
| 3,919,189 | 11/1975 | Empey et al. | 536/114 |
| 3,964,972 | 6/1976 | Patton | 195/31 P |
| 4,010,071 | 3/1977 | Colegrove | 195/31 P |

*Primary Examiner*—Thomas G. Wyse
*Assistant Examiner*—Benoit Castel

[57] ABSTRACT

An aqueous xanthan gum polymer solution that contains bacterial cell bodies can be clarified by enzymatically disintegrating the cell bodies and/or filtering the solution to remove suspended solids. The clarification is improved by initiating an enzymatic disintegration but, before the cell bodies are completely disintegrated, contacting the solution with particles of solid siliceous material at an adsorption-enhancing pH, and then filtering-out the siliceous solids and the partially-disintegrated cell bodies that are adsorbed on them.

6 Claims, 1 Drawing Figure

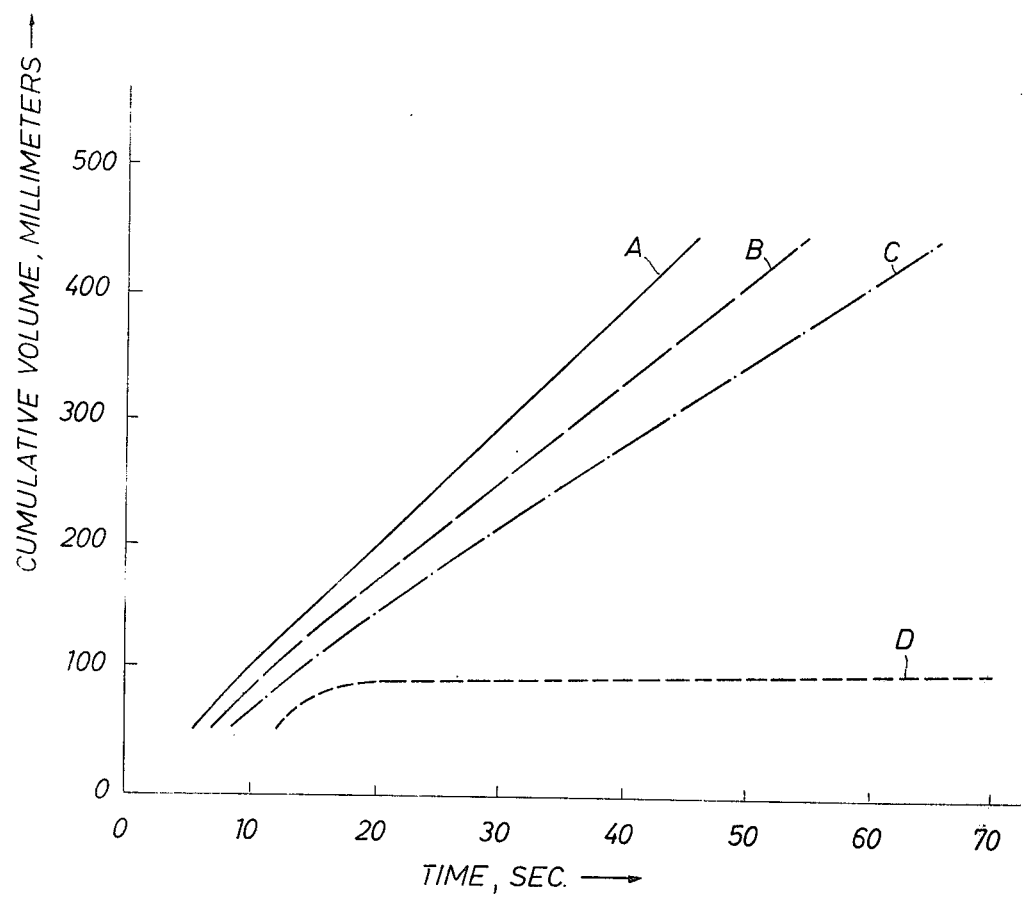

ENZYME-FILTRATION CLARIFICATION OF XANTHAN GUM POLYMER SOLUTION

BACKGROUND OF THE INVENTION

This invention relates to removing solids from aqueous solutions of xanthan gum polymers which contain bacterial cell bodies. It is particularly useful for clarifying such polymer solutions for use as water thickeners in aqueous fluids which are injected into subterranean reservoirs to displace oil.

Numerous procedures have been proposed for clarifying xanthan gum polymer solutions. U.S. Pat. No. 3,966,618 describes treating such solutions with protease enzymes which disintegrate the bacterial cellular debris into water-soluble compounds to an extent such that the polymer solution is clarified. U.S. Pat. No. 3,711,462 describes earlier treatments of such solutions by adding clay particles that are subsequently coagulated and filtered-out so that the cellular bodies are removed along with the coagulated clay particles. U.S. Pat. No. 3,729,460 describes reacting such a debris-containing polymer solution with alkaline materials, at a pH of from about 11.8 to 12.8, to effect a clarification of the solution.

The substantially complete enzymatic disintegration of the cellular bodies tends to convert them to proteinaceous materials which, because they are too finely divided to be removed by filtration, remain in the polymer solution and provide nutrients for bacteria capable of destroying the polymer. The prior non-enzymatic clarification procedures, such as adsorption on coagulated clay particles, or an alkaline treatment prior to a filtration step, tend to be too costly or too difficult for use in waterflooding an oil reservoir.

SUMMARY OF THE INVENTION

The invention relates to improving a xanthan gum clarification process of the type in which a solution containing the biopolymer and bacterial cell bodies resulting from the fermentation, is treated by disintegrating the cell bodies with a protease enzyme and/or filtering the solution through a finely-bedded filter. The improvement comprises initiating an enzymatic disintegration of the bacterial cell bodies but, at a time at which most of the cell bodies have disintegrated only enough to separate them from the polymer, terminating the cell-disintegrating reaction by (a) contacting the solution with siliceous solids, which have surface areas and adsorptive properties at least substantially equivalent to those of a fine sand, at a pH of from about 10-11, which is capable of causing the adsorption of the partially disintegrated cell bodies on the siliceous solids, and (b) filtering-out the siliceous solids and adsorbed cell body materials to an extent such that at least about 80% of the bacterial cell bodies are removed from the polymer solution.

DESCRIPTION OF THE DRAWING

The drawing shows a graph of the cumulative volume with time of the filtrate obtained during the filtration of various aqueous solutions of xanthan gums.

DESCRIPTION OF THE INVENTION

The present invention is, at least in part, premised on the following. The main benefits of a substantially complete enzymatic disintegration of the bacterial cell bodies and/or an enzymatic or alkaline aqueous solution treatment of the bacterial cell bodies coupled with filtration through a fine-pore filter, can be attained while also significantly reducing the time, expense and bacteria-nutrient-retaining disadvantages of such treatments. This is accomplished by limiting the extent of the enzymatic disintegration of the cell bodies, by contacting the solution with relatively coarse silica solids onto which the partially disintegrated cell bodies are adsorbed, at a pH that enhances the adsorption, and the filtering-out of the silica solids and adsorbed cell bodies through a relatively coarse filter. The present procedure provides a relatively rapid and trouble-free filtration. It also avoids the converting of the cell bodies to unfilterably fine proteinaceous material that can serve as a bacterial nutrient. And, it also avoids the problems associated with micro gel formation within the polymer which have been treated with strongly alkaline solutions.

ENZYMATIC HYDROLYSIS OR DISINTEGRATION OF BACTERIAL CELL BODIES

Novo/Alcalase proteolytic enzyme is known to be useful for use in a biopolymer solution clarification process. It is generally preferable to add the enzyme to an aqueous solution into which the polymer is to be dissolved, prior to or along with, the addition of the polymer. Suitable concentrations of the polymer in the aqueous liquid range from about 300 to 8,000 parts per million (parts by weight). Suitable enzyme treating temperatures range from about 30° to 70° C. (86° to 185° F.). As known to those skilled in the art, the severity or completeness of the treatment increases with both time and temperature, and thus the field conditions would generally dictate how the treating times and temperatures should be adjusted for a particular situation.

The enzyme is effective at relatively low concentration. A 6,000 parts per million Kelzan M.F. polymer concentrate can be clarified with 100 parts per million Novo/Alkalase P 1.5 (available from Novo Enzyme Corporation by a substantially complete disintegration of the bacterial cell bodies, within about 45 minutes at 50° C. In such a solution at such a temperature the partial disintegration contemplated by the present invention would be accomplished in about 10 minutes. During the enzyme treatment, the pH of the aqueous solution is preferably from about 7 to 11. In a particular preferred procedure the pH of a relatively soft aqueous liquid (containing less than about 100 parts per million multivalent ion, in terms of calcium ion equivalent) is preferably buffered with a suitable sodium carbonate-bicarbonate system, or where the use of hard water is desired such a system containing a chelating agent such as ethylenediamine tetraacetic acid (EDTA), Diquest 2006 (a salt of an amino tris(methylphosphonic acid) available from Monsanto Chemical Company.

PREFERRED ENZYME TREATMENT

The following procedures are outlined in terms of a laboratory procedure but the principles are generally applicable for field use. Additives, such as an oxygen scavenger, an antioxidant, a buffer for a pH of about 10 to 11, and a bactericidal agent, and the enzyme are added to a good quality relatively soft water, or preferably a soft brine containing from about 50 to 5,000 ppm total dissolved salt. The solution is vigorously stirred, or preferably, is sheared, since the enzyme activity is not lost by a relatively high-shear stirring. In a shearing mixer (e.g., equivalent to a Waring blender at 70 volts on a Variac) the enzyme is preferably added to the buffered brine before or with the biopolymer and the stirring is continued for 10 minutes at 70 volts while the brine solution is maintained at a temperature of from about 50° to 60° C.

COMPARATIVE TESTS OF FILTRATION PROPERTIES

The tests providing the results listed in Tables 1 and 2 compare the filtration properties of biopolymer solutions which were subjected to clarification treatments at concentrations of 6,000 parts per million and then diluted. Table 1 shows the results of comparative tests of filtering aqueous solutions of 300 parts per million Xanflood (xanthan gum polymer available from Kelco Co.) through a 1.2 micron Millipore filter bed (having a diameter of 47 millimeters) under a pressure differential of 20 psi. The data listed under "Filter Calibrations" relate to the times in seconds for filtering distilled water, those listed under "Modified Clarifications Bacterial Bodies Adsorbed on D.E." relate to filtering a solution which was treated as follows. A synthetic reservoir brine containing 160 ppm sodium ion, 20 parts ppm calcium ion, and 10 ppm magnesium ion (from chloride salts), plus 50 ppm sodium sulfite was prefiltered through an 0.45 micron Millipore filter. The pH of the brine solution was adjusted to about 10 by adding sodium hydroxide. While shearing the solution at 70 volts in a Waring blender 100 ppm of Novo/Alkalane P 1.5 enzyme was added. The solution was heated to 60° C. and, while the stirring was continued, 6,000 ppm Xanflood polymer was added. The stirring was continued for 10 minutes, after which particles of J. T. Baker Diatomaceous Earth Filter Aid having a particle size above about 10 microns was added, in an amount providing about 1 gram of the filter aid per 500 grams of the 6,000 ppm biopolymer solution. The stirring was continued for one minute and then the D.E. Filter Aid particles with adsorbed partially disintegrated bacterial cell bodies were filtered out by flowing the solution through a relatively coarse filter having a pore size of about 10 microns. The so-clarified solution was diluted with the synthetic reservoir water to a concentration of 300 parts per million Xanflood and filtered. The data under "Bacterial Bodies Disintegrated Then D.E. Filtered" relate to filtering a solution that was treated in substantially the same way except that the digestion time of the heated polymer and enzyme solution was extended to 1 hour and the filter used had pore sizes of about 1.2 microns.

Table 1

| | FILTERABILITY COMPARISON | | |
|---|---|---|---|
| Cumulative Volume ml | Filter Calibrations Time, Sec. | Modified Clarification Bacterial Bodies Adsorbed on D.E. Time, Sec. | Bacterial Bodies Disintegrated Then D.E. Filtered Time, Sec. |
| 50 | | 7 | 5 |
| 100 | 13 | 13 | 10 |
| 150 | | 20 | 15 |
| 200 | 27 | 28 | 20 |
| 250 | | 36 | 25 |
| 300 | 39 | 46 | 31 |
| 350 | | 56 | 36 |
| 400 | 52 | 69 | 41 |
| 450 | | 85 | 46 |
| 500 | 65 | | |
| Viscosity at 7.3 sec$^{-1}$ | | 4.0 cp | 4.0 cp |

Table 2 shows the filterability of a "Modified Enzyme Clarification" polymer solution treated as described above with 100 parts per million Novo/Alcalase P 1.5 enzyme, at a pH adjusted to between 10.5 to 11 by addition of sodium hydroxide. After the above described D.E. Filter Aid (siliceous solids) addition for bacterial cell body adsorption, the resulting suspension was filtered through a ten-micron teflon Millipore filter to remove the suspended silica particles and materials adsorbed. The so-clarified solution was then diluted to a concentration of 800 parts per million of the Xanflood and filtered through a 1.2 micron Millipore filter.

Table 2

| | FILTERABILITY | |
|---|---|---|
| Cumulative Volume ml | Filter Calibration Time, Sec. | Modified Enzyme Clarification Time, Sec. |
| 50 | | 8 |
| 100 | 13 | 14 |
| 150 | | 21 |
| 200 | 26 | 28 |
| 250 | | 35 |
| 300 | 39 | 43 |
| 350 | | 50 |
| 400 | 51 | 59 |
| 450 | | 66 |
| 500 | 64 | |

The results of such experiments indicate that relatively quick and mild treatments conducted in accordance with the present process provide a very effective clarification of xanthan gum polymer solutions. Such treatments are preferably conducted so that at least about 80% (and preferably at least about 90%) of the bacterial cell bodies were removed by adsorbing them on silica particles which were filtered out. This provides solutions that are advantageously free of substantially all of the proteinaceous material of which the bacterial cell bodies are composed.

The difference in the filterability of solutions treated in accordance with the present process at a pH of from about 10 relative to those treated at a pH of from about 10.5 to 11 are reflected by the results listed in Tables 1 and 2. The solution treated at the lower pH required 85 seconds to yield 450 milliliters of filtrate, whereas only 66 seconds were required for the solution treated at the higher pH.

FILTERABILITY COMPARISONS SHOWN IN THE DRAWING

The drawing shows the volumes of filtrate which were accumulated with time in the course of filtering various xanthan gum polymer solutions each containing about 300 ppm polymer, in substantially equivalent aqueous liquids. Curve A relates to a solution subjected to a substantially complete disintegration of the bacterial cell bodies by an enzyme treatment and a D.E. filteration through a 10-micron Millipore filter. Curve B relates to a solution in which the bacterial cell bodies were similarly disintegrated but no D.E. filteration was applied. Curve C relates to a solution prepared in accordance with the present process, as described in connection with Table 2 above. Curve D relates to a solution to which no clarification treatment was applied.

It is apparent that the present process provides a relatively rapid and efficient method which provides substantially all of the water-thickening and filtration property advantages that are obtainable by the longer duration enzyme treatments and/or filtration procedures. The present process has the added advantage of substantially completely removing the proteinaceous material of which the bacterial cell bodies are composed, whereas an enzyme disintegration of the bacterial cell bodies leaves substantially all of that proteinaceous material in the polymer solution.

VARIOUS ADDITIVES AND TECHNIQUES SUITABLE FOR USE IN THE PRESENT PROCESS

In general, the aqueous liquid used and the concentrations and temperatures at which the enzyme treatment of the xanthan gum polymers are conducted can be substantially equivalent to those described in U.S. Pat. No. 3,966,618. However, in the present process the pH of the solution being treated is preferably maintained at (and/or buffered at) from about 10.5 to 11.

The xanthan gum polymeric materials, the enzymes, the oxygen scavengers, biocides, and the like, can be substantially any of those which are conventionally used in the previously prepared enzyme-treated xanthan gum solutions.

The siliceous materials, for providing surfaces on which the partially disintegrated bacterial cell bodies (which have been separated from the associated polymers by the enzyme treatment) can be adsorbed, can comprise substantially any such particulate and/or fibrous siliceous materials such as sand, glass wool, diatomaceous earth, or the like materials. Such particulate siliceous solids preferably provide surface areas, at least about as great as those of a silica sand of about 100 mesh, and preferably have effective particle sizes at least as great as about 5 (and preferably 10) microns. Particularly suitable materials comprise relatively coarse diatomaceous earth, filter-aid materials having particle sizes of from about 1 to 300 microns. Such materials preferably have sizes equivalent to the Johns-Manville Standard Super Cell material in the 50 micron range.

At the time the siliceous solids are added to or otherwise brought into contact with the polymer and enzyme-containing solution (or at least shortly thereafter), it is important that the pH of that solution be in the order from about 10 to 11. Various procedures can be used for contacting the solution with the siliceous material; for example, the solution can be pumped directly through a sand or glass wool filter in which the siliceous material particle sizes and filtration rate are arranged so that the bacterial debris is adsorbed on the solids and the solids are filtered out as the solution moves through the filters. Where particulate siliceous solids, e.g., diatomaceous earth, filter-aid particles are used, such solids can advantageously be added to a stream of the solution upstream of the filter. In a procedure analogous to that of the "body feed" technique of D.E. filtration. As mentioned above, the pH adjustment can be accomplished by buffering the pH of an aqueous solution of the enzyme, oxygen scavenger, biocides and the like to which the polymer is added.

The filtration of the suspension of siliceous solids and adsorbed bacterial cell bodies from the aqueous xanthan gum and enzyme-containing solutions can be effected by flowing the liquid components through substantially any filter bed means capable of removing the siliceous solids on which the disassociated bacterial bodies are adsorbed. The coarser the filter, the faster the rate. Particularly suitable filtering means comprise relatively coarse diatomaceous earth filters having effective pore sizes of from about 1 to 25 microns.

In the present process the filtration of the suspension of siliceous solids and adsorbed bacterial cell bodies from the aqueous xanthan gum and enzyme-containing solution is improved by making those solutions slightly acetic, e.g., by the addition of a dilute acid such as hydrochloric acid or acetic acid. It has been observed that the improvement provided by such a pH adjustment is exhibited regardless of variations in the polymer solution preparation procedure with respect to extent of shearing, caustic or enzyme treatment, and in spite of an addition of chelating material such as Dequest 2006 or ethylenediamine tetraacetic acid.

Comparative tests were made of the filterabilities of various xanthan gum solutions at various pH's. The procedure used was the following. Kelzan concentrates, 6,000 ppm, were prepared in a Waring blender at 70 volts for 10 minutes in SLBSW containing Alcalase S6.0 or P1.5, 350 ppm eqv. S6.0, and then placed in a water bath at 50° C. for about 2 hours. The SEDPW and SLBSW compositions are given in Table 3. These waters were prefiltered through 0.45μ Millipore M.F. in a Gelman holder at 20 psi. A few of the solutions were also filtered through 5.0μ Millipore.

Kelzan concentrates, 6,000 ppm, prepared by enzymatic clarification and shear mixing in synthetic Lake Blue Steam water and diluted with El Dorado produced water or synthetic El Dorado produced water to 1,000 or 500 ppm polymer and to 80 or 50 percent brine filtered poorly if the solutions were basic. The same stock solution when acidified with either acetic acid or HCl filtered better, see Table 4. The addition of 100 or 200 ppm Dequest 2006 and/or enough EDTA to the SEDPW to complex the multivalent ions did not change the pH dependence of filterability. Addition of $NaHCO_3$ or NaOH making the solutions basic, pH ≅ 7.6, caused a drastic reduction in filtration rate. Substitution of $Ca^{++}$ for $Mg^{++}$ in the SEDPW containing $NaHCO_3$ improved the filterability in mildly basic solution, pH 7.6. Substitution of $Ca^{++}$ for $Mg^{++}$ in the SEDPW did not effect the filterabitity in mildly basic solutions providing $NaHCO_3$ was not present.

Table 3

| SYNTHETIC EL DORADO PRODUCED WATER | | | | | | |
|---|---|---|---|---|---|---|
| Ion | $Ca^{++}$ | $Mg^{++}$ | $Ba^{++}$ | $Sr^{++}$ | $Na^+$ | $K^+$ |
| Concentration ppm | 2,800 | 1,600 | 900 | 590 | 26,670 | 144 |
| | From Chloride Salts | | | | | |

| SYNTHETIC LAKE BLUE STEM WATER | | |
|---|---|---|
| Ion | $Ca^{++}$ | $Mg^{++}$ | Na |
| Concentration ppm | 31.8 | 2.5 | 6.7 |
| | From Chloride Salts | | |

Table 4

| FILTRATION OF KELZAN IN HIGH % (S) EDPW | | | | | | | | | |
|---|---|---|---|---|---|---|---|---|---|
| Sample No. | pH | 1.2μ Filtration Rates ml/sec | Kelzan ppm | (S) EDPW % | $NaHCO_3$ ppm | Acid | NaOH | $Ca^{++}$ Substituted For $Mg^{++}$ | Dequest ppm | EDTA ppm |
| 1 | 7.9 | 50/12, 100/74 | 1,000 | 100 | — | — | X | — | — | — |
| 2 | 7.9 | 100/46, 200/177 | 1,000 | 50 | — | — | X | — | — | — |

Table 4-continued

FILTRATION OF KELZAN IN HIGH % (S) EDPW

| Sample No. | pH | 1.2μ Filtration Rates ml/sec | Kelzan ppm | (S) EDPW % | NaHCO₃ ppm | Acid | NaOH | Ca⁺⁺ Substituted For Mg⁺⁺ | Dequest ppm | EDTA ppm |
|---|---|---|---|---|---|---|---|---|---|---|
| 3 | 7.9 | 100/43, 250/407 | 500 | 50 | — | — | X | — | — | — |
| 4 | 5.6 | 100/16, 250/121 | 1,000 | 80 | — | HCl | — | — | — | — |
| 5 | 6.0 | 100/21, 160/204 | 1,000 | 80 | — | Acetic | — | — | — | — |
| 6 | 6.5 | 100/17, 200/335 | 1,000 | 80 | — | Acetic | — | — | 100 | — |
| 7 | 8.4 | 25/1,176 | 1,000 | 80 | — | — | X | — | 100 | — |
| 8 | 7.6 | 50/670 | 1,000 | 80 | — | — | X | — | 100 | 3,684 |
| 9 | 6.0 | 100/21, 150/114 | 1,000 | 80 | — | Acetic | X | — | 100 | 3,684 |
| 10 | 7.8 | 50/33, 100/234 | 1,000 | 80 | 2,000 | — | — | — | — | — |
| 11 | 6.8 | 100/17, 195/206 | 1,000 | 80 | 2,000 | Acetic | — | — | — | — |
| 12 | 7.7 | 50/10, 100/240 | 1,000 | 80 | 2,000 | — | X | — | 100 | — |
| 13 | 7.6 | 50/18, 150/180 | 1,000 | 80 | 2,000 | — | X | X | — | — |
| 14 | 7.6 | 50/17, 150/196 | 1,000 | 80 | — | — | X | X | — | — |
| 15* | 5.9 | 50/22, 83/990 | 1,000 | 80 | — | HCl | — | — | — | — |

\* = Not Enzyme Clarified
X = Presence of Chemical

What is claimed is:

1. In a xanthan gum polymer solution clarification process in which an aqueous xanthan gum polymer solution that contains bacterial cell bodies is reacted with a protease enzyme, a method for concurrently reducing the treatment time and the bacteria nutritive protein content of the treated solution comprising:

mixing the enzyme and the polymer within an aqueous xanthan gum polymer solution having a temperature from 60° to 70° C., a pH of from about 10 to 11 and containing from about 6,000 to 8,000 ppm of the polymer to initiate the enzymatic disintegration of the bacterial cell bodies;

before about one fourth of the time needed for complete bacterial cell bodies disintegration, and at least as soon as a predominate proportion of bacterial cell bodies have been separated from the polymer but are still substantially intact, terminating the enzymatic cell disintegration by adjusting the pH of the solution to the extent required to provide a pH of from about 10 to 11, contacting the solution with siliceous solids having surface areas and adsorbtivities at least substantially equaling those of a relatively fine sand sized in the order of 100 mesh, adjusting the solution pH to from about 5–7, and filtering out the siliceous solids and adsorbed partially disintegrated bacterial cell bodies by flowing the liquid portion of the polymer solution through a filter that has relatively large effective pore sizes at least equivalent to those of a 10-micron teflon millipore filter but is capable of removing substantially all of the siliceous solids and at least about 80% of the bacterial cell bodies, so that (a) the filtering time is shortened relatively to that obtainable with either a filter having finer pores or with a polymer solution having a higher pH and (b) the so treated solution is substantially free of proteinaceous material formed by the enzymatic disintegration of bacterial cell bodies.

2. The process of claim 1 in which the siliceous solids which are mixed with the enzyme-containing solution of polymer comprise diatomaceous earth particles having average sizes of from about 1 to 300 microns.

3. The process of claim 1 in which the aqueous liquid within which the polymer and enzyme are mixed to form said polymer solution is a relatively soft brine having a total dissolved solids content of from about 50 to 5,000 ppm.

4. The process of claim 3 in which the aqueous liquid contains an oxygen-scavenging amount of dissolved sulfite and catalyst.

5. The process of claim 4 in which the aqueous liquid is prefiltered prior to the addition of the enzyme.

6. The process of claim 3 in which the aqueous liquid contains a carbonate-bicarbonate buffer system for maintaining the pH at from about 10 to 11.

* * * * *